United States Patent
Sekine et al.

(10) Patent No.: US 7,105,155 B2
(45) Date of Patent: Sep. 12, 2006

(54) METHOD AND ACTIVATED LYMPHOCYTE PREPARATIONS FOR PREVENTING RECURRENCE OF CARCINOMA

(75) Inventors: Teruaki Sekine, Koto-ku (JP); Tadatoshi Takayama, Suginami-ku (JP)

(73) Assignee: Lymphotec, Inc, Tokyo (JP)

( * ) Notice: Subject to any disclaimer, the term of this patent is extended or adjusted under 35 U.S.C. 154(b) by 0 days.

(21) Appl. No.: 09/944,360

(22) Filed: Sep. 4, 2001

(65) Prior Publication Data

US 2003/0044387 A1 Mar. 6, 2003

(51) Int. Cl.
*A61K 35/00* (2006.01)

(52) U.S. Cl. .................. 424/93.1; 424/93.7; 424/277.1; 424/184.1

(58) Field of Classification Search ................ 424/93.1, 424/93.7, 534, 277.1, 184.1; 435/7.1
See application file for complete search history.

(56) References Cited

FOREIGN PATENT DOCUMENTS

JP          3-80076       4/1991

OTHER PUBLICATIONS

Takayama et al, Sep. 2, 2000, The Lancet, 356: 802-807.*
Sekine et al. 1994, Human cell, The Japan human cell socielty, 7(3): 121-124. English translated version.*
Sasaki Y et al, J Hepato-biliary-pancreatic surgery, 1998, 5(1): 14-17.*
Montesano, R et al, 1996, Intl J Cancer, 69(3): 225-235.*
Burmer, GC et al, 1991, Environmental Health perspectives, 93: 27-31.*
Busken, C et al, Digestive Disease Week Abstracts and Itinerary Planner, 2003, abstract No. 850.*
Sekine T, 1994, Human cell: Official J human cell res society (Japan): 7(3):121-4.*
Chakravarty, Ashim K, 1997, Current Science (Bangalore) 73(2): 201-203.*
T. Takayama et al., "Adoptive Immunotherapy to Lower Postsurgical Recurrence Rates of Hepatocellular Carcinoma: a Randomised Trial", The Lancet, vol. 356, No. 9232, Sep. 2, 2000, pp. 802-807.

* cited by examiner

*Primary Examiner*—Jeffrey Siew
*Assistant Examiner*—Minh-Tam Davis
(74) *Attorney, Agent, or Firm*—Wenderoth, Lind & Ponack, L.L.P.

(57) ABSTRACT

Activated lymphocytes are administered to a cancer patient at least five or more times within eight months after performing surgical and chemotherapeutic treatment or radiotherapy for treating cancer particularly liver cancer, so that recurrence of the cancer can be prevented over a long period of five or more years. The activated lymphocytes to be administered while performing treatment of cancer may be autologously derived from a cancer patient or collected from the other cancer patient at need. The activated lymphocytes can be cultivated for proliferating or activating lymphocyte cells collected in the presence of solid-phase anti-CD3 antigen and interleukin 2.

5 Claims, No Drawings

METHOD AND ACTIVATED LYMPHOCYTE PREPARATIONS FOR PREVENTING RECURRENCE OF CARCINOMA

BACKGROUND OF THE INVENTION

1. Field of the Invention

This invention relates to a method for preventing recurrence of carcinoma and cancer over a long term and preparations containing activated lymphocytes for preventing recurrence of carcinoma and cancer over a long term, and more particularly to a long-term prophylactic method and longterm prophylactic preparations capable of preventing recurrence of carcinoma and cancer over a span of at least five years or more.

2. Description of the Prior Art

The inventors of the present invention have already reported that lymphocytes can be proliferated with solid-phase anti-CD3 antigen and interleukin 2 so as to have an antitumor function. (Japanese Patent Application Public Disclosure HEI 3-80076(A))

The report makes it clear that the lymphocytes have the effectiveness of preventing recurrence of cancer and improving antitumor activation within about one to two years. However, even if the lymphocytes are solely used, recurrence of cancer cannot substantially be prevented with clinical significance over a long term of five years or more, on the basis of which an assessment of the therapeutic value of the lymphocytes is made.

Further, the report-indicates that use of the activated lymphocytes enables prevention of recurrence of cancer. However, a long-term prevention of recurrence of carcinoma cannot be guaranteed in the report.

There have been known medical techniques of proliferating lymphocytes derived from peripheral blood or the like with anti-CD3 antigen and interleukin 2 to be effective against pulmonary carcinoma in chemotherapy and freezing the lymphocytes so as to thaw and proliferate the frozen lymphocytes in use. S. A. Rosenberg reported that LAK cells activated with interleukin 2 has antitumor activity, but has not clarified on whether or not the LAK cells have a function of preventing recurrence of carcinoma.

However, the efficacy of preventing recurrence of carcinoma and the antitumor activity last only for a short period of about two years according to the conventional treatment using the activated lymphocytes as described above. Even by taking surgical or chemotherapeutic treatment or radiotherapy along with administration of the activated lymphocytes, the efficacy of preventing recurrence of carcinoma could not last to five or more years. Although chemotherapeutic agents or preparations, which have been widely used as most popular therapeutic measures effective against cancer, generally have an antitumor efficacy (function of diminishing cancer), they have little therapeutic value of preventing recurrence of carcinoma without producing harmful side effects.

OBJECT OF THE INVENTION

An object of the present invention is to provide a method capable of preventing recurrence of carcinoma or cancer for at least five years when applied in combination with surgical or chemotherapeutic treatment or radiotherapy without administering solely lymphocytes to a cancer patient.

Another object of the present invention is to a method capable of substantially preventing recurrence of carcinoma or cancer without causing harmful side effects by jointly using activated lymphocytes autologously derived from a cancer patient himself or collected from the other cancer patient than the patient to be treated within a prescribed period of time after subjecting the cancer patient, specifically liver cancer, to surgical or chemotherapeutic treatment or radiotherapy, and lasting the efficacy of treatment for a long period of at least five or more years.

Still another object of the present invention is to provide preparations containing activated lymphocytes for preventing recurrence of carcinoma or cancer for a long period of at least five or more years, which are used along with surgical or chemotherapeutic treatment or radiotherapy without administering solely lymphocytes to a cancer patient.

SUMMARY OF THE INVENTION

To attain the objects described above according to the present invention, there is provided a method for preventing recurrence of carcinoma or cancer for a long period of time, in which activated cymphocytes are administered while treating cancer.

Specifically, the treatment according to the method of the invention is effective against liver cancer. This treatment includes surgical or chemotherapeutic treatment and radiotherapy. The activated lymphocytes to be administered while treating the cancer may be prepared by autologously deriving lymphocytes from a patient himself or collecting lymphocytes from the other cancer patient than the patient to be treated and then proliferously cultivating the lymphocytes thus derived or collected. As another measures, the lymphocytes may be collected from the cancer patient himself or the other cancer patient at need. The activated lymphocytes to be administered to the cancer patient, which are used while treating the cancer, may be prepared from the lymphocytes collected from the cancer patient himself or the other cancer patient. The activated lymphocytes can be obtained by the proliferating cultivation process or activating cultivation process in the presence of solid-phase anti-CD3 antigen and interleukin 2.

The preparations capable of preventing recurrence of carcinoma or cancer for a long period of time according to the present invention are prepared from the cancer patient and administered to the cancer patient in performing the treatment of cancer. The preparations can be obtained by cultivation to proliferate or activate lymphocytes in vitro.

DESCRIPTION OF THE PREFERRED EMBODIMENTS

The method and preparations for preventing recurrence of carcinoma and cancer over a long term according to the present invention will be described hereinafter.

The method of the invention is practiced while carrying out proceedings of treating cancer, specifically liver cancer and preventing recurrence of cancer with administration of activated lymphocytes, so that a complete therapeutic effect can be attained to prolong the effect of preventing recurrence of cancer for a long period of at least five or more years. In concrete terms, the present invention is featured in that the treatment of cancer according the invention is performed along with administration of the preparations made from the activated lymphocytes of the invention.

The "treatment of cancer" as termed herein has principally a meaning of a surgical operation. Thus, the efficacy of preventing recurrence of cancer for a long period of at least five or more years can be secured by administering the activated lymphocytes to the cancer patient several times. The treatment of cancer may imply not only the surgical operation noted above, but also chemotherapeutic treatment and radiotherapy.

[Collecting of Lymphocyte Cells]

The collection of lymphocyte cells is carried out when need arises in principle. The lymphocyte cells are prepared by segregating lymphocytes from the peripheral blood of a cancer patient himself to be treated or the other cancer patient than the cancer patient to be treated.

In such a case, it is preferable to collect the lymphocyte cells of more than $1 \times 10^9$ per milliliter, resulting in an improvement in efficacy of preventing recurrence of cancer. The peripheral blood is preferably collected from a vein. A desirable amount of blood collected in one operation is on the order of 0.01 to 100 ml, but it is not specifically limited. However, in order to alleviate a physical burden on a donor in collecting the blood and facilitate labor of collecting the blood and segregating lymphocyte cells from the blood, it is desirable to collect about 5 to 50 ml of peripheral blood in one operation, more preferably 10 to 20 ml of blood. In collecting the blood, heparin or citric acid may be added to the collected blood so as to prevent the collected blood from coagulating. The segregation of the lymphocyte cells from the peripheral blood thus collected may be fulfilled by a common segregating method for lymphocyte cells such as a discontinue density gradient centrifugation using sucrose, a lymphocyte separator available on the market or other agents.

[Proliferation of Lymphocyte Cells]

Next, proliferation and cultivation of cells collected in the manner as noted above will be described. The proliferation of the lymphocyte cells according to the invention is carried out by proliferating cultivation or activating cultivation in the presence of a combination of solid-phase anti-CD3 antigen and interleukin 2. In the cultivation, the lymphocyte cells may be suspended in a culture medium containing interleukin 2 to be cultivated in a culture in a culture kit with addition of solid-phase anti-CD3 antigen. In this case, various types of mitogen growth factors or activating factors may be used in proliferating and activating the cells at need.

Any type of anti-CD3 antigen capable of hastening the proliferation and activation of the lymphocyte cells may be used. That is, the type of the anti-CD3 antigen is not specifically limited in the invention. The anti-CD3 antigen used for stimulating the lymphocyte cells may be yielded in an animal or cells by use of refined CD3 molecules, or there may be advantageously used commercial OKT-3 antigen (produced by Ortho Pharmaceutical) from the viewpoint of cost and stability.

It is desirable to use the anti-CD3 antigen in its solid phase in consideration in the light of the efficiency of proliferating and handling the lymphocyte cells. There may be used implements made of glass, polyurethane, polyolefine, polystyrene or the like for solidifying the antigen, or a sterilized cell-cultivating plastic flask, which is easy to obtain at the market. The size of the flask may be arbitrarily determined.

It is desirable to prepare the anti-CD3 antigen by placing dilute solution of anti-CD3 antigen into a solidifying implement and permitting it to stand in its solid phase at temperatures of, for example, 4° C. to 37° C. for 2 to 24 hours. In solidifying, the anti-CD3 antigen may be preferably diluted with physiological saline solution such as sterized Dulbecco's phosphate buffered saline solution into concentrations of 1 to 30 μg/ml. After solidifying, the anti-CD3 antigen may be preserved in a cold room or refrigerator (4° C.) until use. When used, the physiological saline solution is removed from the anti-CD3 antigen, and the anti-CD3 antigen may be rinsed out with Dulbecco's phosphate buffered saline solution at normal temperature, as occasion demands.

It is preferable to put interleukin 2 into the culture solution to improve the efficiency of proliferation. The commercial interleukin 2 available on the market may be desirably used in concentrations of from 1 to 2000 U/ml. The interleukin 2 may be dissolved in a culture solution for cultivating cells, which has been widely used in this field of art, such as water, physiological saline solution, Dulbecco's phosphate buffered saline solution, RPMI-1640, DMEM, IMDM and AIM-V The interleukin 2 once dissolved may be preferably cryopreserved to prevent deterioration of activity thereof.

In this case, any type of culture solution suitable for cultivation of the lymphocyte cells may be used, and therefore, the type of the culture solution is not specifically limited in the invention. That is, there may be suitably used a culture solution derived from an organism, such as serum, and a synthetic medium prepared by adding amino acid, vitamin, uncleic acid base or the like to an equilibrium saline solution. As the suitable culture solution in this case, there may be enumerated, for example, RPMI-1640, AIM-V, DMEM and IMDM. In specific, of these solutions, RPMI-1640 is most suitable. It is desirable to add normal human serum to the culture medium, resulting in producing an excellent effect of proliferating the lymphocytes. The culture medium available at the market may be used.

The cultivation in the invention can be fulfilled by an ordinary cell cultivating method. For instance, the cultivation may be practiced in a $CO_2$-incubator. It is desirable to carry out the cultivation at the $CO_2$-concentration of 1 to 10%, preferably 5%, at temperatures of 30° C. to 40° C., preferably about 37° C.

[Administration of Activated Lymphocytes]

The more the frequency of administering the activated lymphocytes is, the higher the therapeutic efficacy becomes. However, the administration of the activated lymphocytes to a cancer patient is generally made every several days to several months. The administration of the activated lymphocytes may commence not only after conducting an operation of surgical removal, chemotherapeutic treatment or radiotherapy, but also at the earliest possible time before taking surgical or chemotherapeutic treatment or radiotherapy, so that the efficacy of preventing recurrence of cancer can be more improved. It is desirable to continue administering the activated lymphocytes to the cancer patient over about five years after the operation, if possible. However, in general, even short term administration of the activated lymphocytes for six months to eight months after the operation can securely produce a sufficient effect of preventing recurrence of cancer for the following five or more years.

In general, the administration of the activated lymphocytes may possibly be made 1 to 1000 times. However, the administration made once has relatively little effect. Thus, in order to stably produce the stable effect of preventing recurrence of cancer for five or more years after conducting the operation of treating the cancer, it is required to administer the activated lymphocytes to the patient in therapy at least five or more times within eight years after the operation for the cancer. That is, the more the frequency of administering the activated lymphocytes to the patient is, the higher the effect of preventing recurrence of cancer becomes. In either way, the conditions of the frequency of administering the activated lymphocytes, the period of time within which the activated lymphocytes are administered, and the number of times the administration is made may be arbitrarily determined according to circumstances.

In the method of the invention, the administration of the activated lymphocytes is performed while proceeding with the treatment for cancer. Further, according to the invention, from the activated lymphocytes prepared in the manner as described above, there can be produced long-term prophylactic preparations capable of preventing recurrence of cancer, particularly liver cancer. The activated lymphocytes to be administered to the cancer patient while treating the cancer can be cultivated in vitro to be proliferated or activated. According to this method, the efficiency of cultivating the lymphocytes can be remarkably improved to obtain homogeneous and stable lymphocytes activated.

The lymphocytes thus proliferated and activated can be administered mainly to a patient of liver cancer, consequently to be effective for preventing recurrence of cancer over a long period of five or more years after the operation for the cancer. However, the present invention does not contemplate imposing any limitation on the subject to be treated. That is, the prophylactic preparations according to the present invention have the beneficial efficacy of preventing recurrence of not only liver cancer, but also lung cancer, stomach cancer, colon cancer, rectal cancer, pancreatic cancer, gallbladder cancer, ovarian cancer, uterine cancer, testis cancer, prostate cancer, leukemia, sarcomas, brain tumor and other carcinomas.

EMBODIMENTS

[Segregation of Lymphocytes]

From the vein of a patient of liver cancer, 20 to 50 ml of the peripheral blood was drawn with addition of heparin by using a syringe. A hypodermic needle was aseptically taken off from the syringe containing the blood thus drawn in a clean bench (Model S-1100 made by Showa Science Co., Ltd.) without touching the joint portion between the syringe and needle and replaced with another hypoderic needle (19G×1-½" needle made by Nipro Medical Corporation). Then, rinsing culture medium (made by Nikken Bio Medical Laboratory Inc.) was put equally by 15 ml into two centrifugal settler tubes of volume 50 ml (Product No. 2341-050 made by Iwaki Glass Co., Ltd.) Thereafter, the blood collected in each centrifugal settler tube was diluted three times with a culture solution to obtain equivalently diluted blood.

Thereafter, each of the centrifugal settler tubes was tightly covered with a lid, and then, turned upside down several times to mingle. Then, into six centrifugal settler tubes each of 15 ml in volume, 15 ml of Lymphosepar-I (made by Immuno-Biological Laboratories Co., Ltd.) were transfused by using a pipette of 10 ml in capacity (Pipette 4105 imported and sold by Corning International). Then, 10 ml of blood diluted with the rinsing culture medium were slowly poured into the respective centrifugal settler tubes, so as not to disturb the surface of the solution in each tube and thereafter, centrifuged at a relatively low speed of 1800 rpm at a centrifugal separating temperature of 20° C. for 15 minutes with a centrifugal separator with its brakes off. (A centrifugal settler H-700R made by Kokusan Co. Ltd. was used.)

After centrifugal sedimentation, the supernatant liquid of the liquid contents centrifuged in each of the tubes was slowly sucked up to a depth of about 1 cm above the lymphocyte layer centrifugally precipitated in each tube in an aseptic condition by using an aspirator so as not to suck in the lymphocyte cells. Then, the layer of the lymphocyte cells in the tube was sucked up by using a pipette of 5 ml in capacity so as not to suck in blood clots and collected with a centrifugal settler tube of 50 ml in capacity, in which 25 ml of rinsing culture medium (RPM1640+6) were contained in advance. Then, the centrifugal settler tube was covered with a lid and turned upside down several times to mingle. Thereafter, the centrifugal settler tube was centrifuged at 1800 rpm at a centrifugal separating temperature of 20° C. for 10 minutes. After each of the centrifugal settler tube was further centrifuged, the supernatant liquid in the tube was removed and thoroughly dispersed by using a vortex mixer.

In each tube, 44 ml of culture medium (RPMI1640+7 made by Nikken Bio Medical Laboratory Inc.) containing 35,000 U/ml of IL-2 (made by Cetus Corporation) and 5 ml of human serum were added to 50 ml of culture medium (often abbreviated as "medium") and thoroughly mixed by repeatedly turning the tube upside down to obtain cell suspension. Then, the cell suspension was put by 10 µl into tubes (Product 72,690 imported and sold by K. K. Asist) and mixed with 40 µl of Turk's solution (made by Muto Kagaku Yakuhin) in each tube. The mixtures thus obtained were applied by 10 µl to a hemocytometer (Product No. 9731 made by Perkin-Elmer Corporation) and measured to count the number of cells under a microscope (Model 211320 made by Olympus Optical Co., Ltd.) There were obtained the results that the total numbers of the cells in the tubes were in the range of $1.0 \times 10^7$ to $7.0 \times 10^7$.

[Arrangement of Flask Containing Solid-phase OKT3]

A solution consisting of 5 µl of OKT3 (imported and sold by Janssen-Kyowa Co., Ltd. and produced by Ortho Pharmaceutical) prepared previously with 8 µl of PBS(−) was poured by 10 µl into a cultivating flask having the base area of 225 $cm^2$ (MS-2080R made by Sumitomo Bakelite Company Ltd.) so as to uniformly soak the bottom of the flask in the solution. OKT3 in the flask was sucked out by an evacuator on the next day. Then, Upon pouring 50 ml of PSB(−) into the flask, the flask kept covered was vehemently shaken, and thereafter, opened to take out the solution. Again, 50 ml of OKT3 was added into the flask, and then, upon covering the flask with the lid, the flask was vehemently shaken. Thereafter, the flask was opened and remaining liquid contents were courteously removed from the flask and lid, thus to prepare a flask containing solid-phase OKT3.

[Cultivation for Activating Lymphocytes]

To the flask containing solid-phase OKT3 prepared in the "flask arrangement" process described above, 50 ml of cell suspension obtained in the aforesaid "lymphocyte segregation" process was distributed. Then, cultivation in the flask was performed at 37° C. in the presence of carbon dioxide gas having a concentration of 5%. After five days, 50 ml of culture medium was added, and the cultivation was continued at 37° C. in the presence of carbon dioxide gas having a concentration of 5%. After the following four days, 150 ml of culture medium was added, and further cultivation was performed at 37° C. in the presence of carbon dioxide gas having a concentration of 5%. For two more days, the cultivation was continued at 37° C. in the presence of carbon dioxide gas having a concentration of 5%. Consequently, $2.0 \times 10^8$ to $7.0 \times 10^8$ of activated lymphocytes could be obtained.

[Cultivation for Growing Lymphocytes]

The lymphocytes prepared in the aforementioned "lymphocyte activating cultivation" process was transfused to a cultivating gas-permeable bag containing 750 ml of culture medium LL-7 (made by Nikken Bio Medical Laboratory Inc.) or Medium 930 (made by Kohjin Bio Co. Ltd.) and cultivated at 37° C. in the presence of carbon dioxide gas having a concentration of 5% in a carbon dioxide incubator (Model CDP-300A made by K. K. Hirasawa). After two days, the cultivating gas-permeable bag ("Nipro Culture Bag A-1000" made by Nipro Medical Corporation) containing the cells and another cultivating gas-permeable bag containing new culture medium were joined to each other by a germfree connector (made by Terumo Corporation). Upon fully mixing the culture medium in the joined gas-permeable bags, the joined bags were cut apart, and the cut portions of the bags were aseptically sealed. Thereafter, cultivation was performed at 37° C. in the presence of carbon dioxide gas having a concentration of 5%.

After two more days, the lymphocyte cells were cultivated by using two gas-permeable bags in which the cultivation was continued and two other gas-permeable bags each containing new culture medium having the cells dispersed uniformly. That is, the cultivation was carried out by using the four gas-permeable bags. After the following two days, cultivation was performed by using the aforesaid four gas-permeable bags containing the cells and two new gas-permeable bags having the cells dispersed uniformly therein.

[Production of Preparations to be Administered]

The culture mediums containing the cells in three to six of the aforementioned gas-permeable bags were transfused into 250 ml centrifuge tubes (made by Corning International) to centrifugally segregate the cells. Then, rinsing of the cells was carried out by removing the culture solutions from the tubes by decantation, adding physiological saline solutions to cell pellets to suspend the cells in the solutions, and subjecting the cells to centrifugal segregation. Further, the same rinsing was carried out by physiological saline solution containing 0.1% of human albumin instead of the aforesaid physiological saline solution, thus to prepare cell pellets.

To the aforesaid cell pellets, 200 ml of physiological saline solution containing 2% of human albumin were added to allow the cell pellets to be suspended therein. Lastly, the desired preparations to be administered to a cancer patient were prepared by filtrating the solution through a stainless wire filter of 100µ in mesh and packing it into a blood transfusion bag. In this case, the number of cells packed in the blood transfusion bag was $6 \times 10^9$ to $20 \times 10^9$.

[Administration of the Preparations]

The preparations produced in the aforesaid "production" process were inoculated into the vein of the liver cancer patient from which the blood was drawn in the "segregation" process described above. The administration of the preparations was performed three times within three weeks after performing an operation for the liver cancer, and after three and six months from the operation for the cancer. Namely, the preparations according to the invention were administered to the patient of liver cancer five times in total.

[Judgment of the Effect of Preventing Recurrence of Cancer]

An analysis to determine the rate of recurrence of cancer from the commencement of the treatment until five years after the operation for cancer was performed on forty-nine cases dosed with the activated lymphocytes according to the invention and fifty-two cases who did not dosed with the activated lymphocytes. It was evident from the result of the analysis that the relapse-free survival of the latter (cases dosed with no activated lymphocyte) was 21%, but the relapse-free survival of the former (cases dosed with the activated lymphocytes of the invention) was 35%. Thus, there could be recognized a significant difference therebetween based on a probability level of 1%. Of the cases dosed with the activated lymphocytes of the invention, no case was caught by serious harmful side effects, and some cases became slightly feverish. That is, the result of the analysis reveals that the activated lymphocytes according to the invention have the excellent efficacy of preventing recurrence of cancer (in particular, liver cancer) for a long period of at least five or more years, and besides, the activated lymphocytes of the invention has very little side effects.

Next, one example of cryopreserving the activated lymphocytes prepared in the aforementioned "production" process will be described. Upon centrifuging the activated lymphocytes obtained in the "production" process, the culture medium is removed by decantation to obtain cell pellets. To the cell pellets, 18 ml of cell preserving solution (prepared by mixing 5 ml of human serum, dimethyl sulfoxide (made by Nacalai Tesque, Inc., hereinafter abbreviated as "DMSO") with 40 ml of culture medium (RPMI1640+7)) is added. After fully mixing the mixture thus obtained, it is distributed by 3 ml into five cell preserving tubes of 5 ml in capacity (imported and sold by Corning International) ($5 \times 10^7$ per tube). The cell preserving tubes thus prepared are placed in a superthermal freezer and preserved at −80° C.

In thawing the frozen lymphocyte cells, the tubes are taken out from the freezer and warmed with a heat block (Model TAL-1G made by Tietech Co. Ltd.) at 37° C. for four minutes to thaw and restore the frozen lymphocyte cells. The lymphocyte cells thus thawed and restored are aseptically transfused by 3 ml into a centrifugal settler tubes of volume 50 ml, and 10 ml of physiological saline solution is added thereto to produce suspension. After centrifuging the suspension (at 1000 rpm at 20° C. for 5 minutes), supernatant liquid in the tube is removed by decantation, and further, 10 ml of physiological saline solution is added to produce suspension. Again, after centrifuging the suspension (at 1000 rpm at 20° C. for 5 minutes), supernatant liquid is removed by decantation, and 10 ml of physiological saline solution is added to suspend the cells therein. Once again, after centrifuging the suspension (at 1000 rpm at 20° C. for 5 minutes), supernatant liquid is removed by decantation, and 5% of human serum albumin is added to suspend the cells therein, so that the desired preparations to be administered to a cancer patient can be obtained.

What is the biggest fear of cancer is a recurrence of the cancer. Assuming that there is no recurrence of cancer, the majority of cancers can easily be treated. From this viewpoint, the long-term prophylactic method capable of preventing recurrence of cancer over a span of at least five years or more according to the present invention brings about an epoch-making efficacy of curing cancer completely. As is described above, in the prophylactic method according to the invention, the activated lymphocytes which are prepared by segregating the lymphocyte cells from the peripheral blood from the cancer patient to be treated or other cancer patient are administered at least five or more times within eight months after the commencement of surgical or chemotherapeutic treatment or radiotherapy with carcinostatic for cancer, specifically liver cancer. According to the prophylactic method of the invention, an excellent synergistic effect brought about by the efficacies of curing the cancer and preventing recurrence of cancer over a long period of time can be obtained. It was confirmed that the efficacies of the preparations according to the invention are extremely effective against cancer, particularly liver cancer.

In cases that the cancer is not completely removed surgically, the efficacy of suppressing development of the cancer according to the invention was confirmed clinically. The prophylactic method and preparations according to the present invention are very effective for not only human, but also pets such as dog and cat, livestock such as cattle, pig, sheep and horse, and other animals, and can prevent recurrence of cancer in these organisms over a long period of time.

Although the invention has been described in its preferred form with a certain degree of particularity, it is understood that the present disclosure of the preferred form has been changed in the details of construction and the combination and arrangement of parts may be resorted to without departing from the spirit and the scope of the invention as hereinafter claimed.

What is claimed is:

1. A method for preventing recurrence of liver cancer for five years, which comprises administering a therapeutically effective amount of activated lymphocytes to a liver cancer patient in need thereof while performing surgical treatment of liver cancer, resulting in the prevention of recurrence of liver cancer for five years, wherein said activated lymphocytes are produced by collecting lymphocytes from the patient having liver cancer or another patient having liver cancer and cultivating the collected lymphocytes in the presence of solid-phase anti-CD3 antigen and interleukin 2 before administration.

2. The method as set forth in claim 1, wherein said activated lymphocytes are collected from the patient having liver cancer.

3. The method as set forth in claim 1, wherein said activated lymphocytes are administered at a concentration of more than $1 \times 10^9$ cells/ml.

4. The method as set forth in claim 1, wherein said activated lymphocytes are administered within eight months after commencing said surgical treatment of liver cancer.

5. The method as set forth in claim 1, wherein said activated lymphocytes are administered at least five or more times within eight months after commencing said surgical treatment of liver cancer.

* * * * *